US008367748B2

(12) United States Patent
Moszner et al.

(10) Patent No.: US 8,367,748 B2
(45) Date of Patent: Feb. 5, 2013

(54) SURFACE-MODIFIED FILLERS

(75) Inventors: Norbert Moszner, Triesen (LI); Simone Klapdohr, Rankweil (AT); Ulrich Salz, Lindau (DE); Jorg Zimmermann, Lustenau (AT); Volker M. Rheinberger, Vaduz (LI)

(73) Assignee: Ivoclar Vivadent AG, Schaan (LI)

( * ) Notice: Subject to any disclaimer, the term of this patent is extended or adjusted under 35 U.S.C. 154(b) by 1178 days.

(21) Appl. No.: 11/292,578

(22) Filed: Dec. 2, 2005

(65) Prior Publication Data

US 2006/0247329 A1 Nov. 2, 2006

(30) Foreign Application Priority Data

Apr. 27, 2005 (DE) .......................... 10 2005 019 600

(51) Int. Cl.
*A61K 6/083* (2006.01)
*C08K 9/06* (2006.01)
*A61C 5/00* (2006.01)

(52) U.S. Cl. ..... 523/117; 523/116; 523/202; 433/228.1; 106/35

(58) Field of Classification Search .................. 523/117, 523/116, 202; 433/228.1
See application file for complete search history.

(56) References Cited

U.S. PATENT DOCUMENTS

| | | | | |
|---|---|---|---|---|
| 3,249,461 | A | | 5/1966 | Grotenhuis |
| 4,148,637 | A | * | 4/1979 | Kubota et al. .................... 430/66 |
| 4,220,582 | A | | 9/1980 | Orlowski et al. |
| 4,349,388 | A | * | 9/1982 | Marzocchi et al. ........... 428/391 |
| 4,434,210 | A | * | 2/1984 | Nakajima et al. .............. 428/447 |
| 5,055,497 | A | * | 10/1991 | Okada et al. ................... 523/116 |
| 5,367,002 | A | | 11/1994 | Huang et al. |
| 5,871,360 | A | | 2/1999 | Kato |
| 6,214,101 | B1 | | 4/2001 | Nakaseko |
| 6,300,389 | B1 | * | 10/2001 | Sato et al. ...................... 523/116 |
| 6,384,104 | B1 | * | 5/2002 | Chang et al. ................... 523/105 |
| 6,387,981 | B1 | | 5/2002 | Zhang et al. |
| 6,417,244 | B1 | | 7/2002 | Wellinghoff et al. |
| 6,689,823 | B1 | * | 2/2004 | Bellare et al. .................. 523/115 |
| 7,041,709 | B2 | * | 5/2006 | Klee et al. ........................ 522/99 |
| 7,622,538 | B2 | * | 11/2009 | Moszner et al. ............... 526/307 |
| 2002/0065337 | A1 | | 5/2002 | Pflug |
| 2002/0072551 | A1 | | 6/2002 | Han et al. |
| 2002/0152930 | A1 | * | 10/2002 | Neubert et al. ................... 106/35 |
| 2003/0004294 | A1 | * | 1/2003 | Moszner et al. ................. 528/10 |
| 2003/0187094 | A1 | | 10/2003 | Klee et al. |
| 2004/0010055 | A1 | | 1/2004 | Bui et al. |
| 2005/0175796 | A1 | * | 8/2005 | Nakamura et al. ........... 428/32.8 |
| 2006/0041035 | A1 | | 2/2006 | Poppe et al. |
| 2009/0186960 | A1 | * | 7/2009 | Moszner et al. ............... 523/116 |
| 2009/0209722 | A1 | * | 8/2009 | Jiang et al. ....................... 528/25 |

FOREIGN PATENT DOCUMENTS

| | | |
|---|---|---|
| DE | 24 05 578 A1 | 8/1975 |
| DE | 32 47 800 A1 | 7/1983 |
| DE | 32 10 775 A1 | 9/1983 |
| DE | 33 13 819 A1 | 10/1984 |
| DE | 273 846 A1 | 11/1989 |
| DE | 40 29 230 A1 | 3/1992 |
| DE | 689 04 665 T2 | 3/1993 |
| DE | 43 23 143 C1 | 12/1994 |
| DE | 195 08 586 A1 | 9/1996 |
| DE | 298 05 847 U1 | 5/1999 |
| DE | 100 18 405 A1 | 10/2001 |
| DE | 102 34 326 B3 | 2/2004 |
| DE | 600 11 122 T2 | 7/2004 |
| EP | 0 333 503 A2 | 9/1989 |
| EP | 0598441 A2 | 5/1994 |
| EP | 0 909 761 B1 | 4/1999 |
| EP | 1 190 695 A1 | 3/2002 |
| GB | 1 488 403 | 10/1977 |
| JP | 2028204 A | 1/1990 |
| JP | 4242240 A | 8/1992 |
| JP | 5295294 A | 11/1993 |
| JP | 6234892 A | 8/1994 |
| JP | 2005517719 T | 6/2005 |
| JP | 2006502949 T | 1/2006 |
| WO | WO 98/13008 | 4/1998 |
| WO | WO 00/69392 | 11/2000 |
| WO | 03070198 A1 | 8/2003 |
| WO | WO 2004/004669 A1 | 1/2004 |
| WO | 2004035649 A1 | 4/2004 |
| WO | WO 2005/002530 A1 | 1/2005 |
| WO | WO 2005/011621 A1 | 2/2005 |

OTHER PUBLICATIONS

Calgon Corp., "Abstract 41318f: Acrylic Polymer Scale Inhibitors," *Chemical Abstracts* 107:41313 (1987) (JP 62 53,314).
Guillet, "Treatment of Fillers with Organofunctional Silanes, Technology and Applications,"*Macromol. Symp.* 194:63-74 (2003).
Mansri et al., "Nouveaux Polymères Styréniques á Chaînes Latérales Céto-Énol-I. Synthèse Et (Co)Polymérisations De β-Dicétones Monomères," *Eur. Polym. J.* 32(3):269-275 (1996).
Plueddemann, "Silane Coupling Agents," Plenum Press, $2^{nd}$ Ed., New York and London (1991) (Table of Contents only).
Teyssié & Smets, "Synthesis and Polymerization of Methacroylacetone," *Makromol Chem.* 26:245-251 (1958).
Pape & Plueddemann, "Improvements in Silane Coupling Agents for More Durable Bonding at the Polymer-Reinforcement Interface," *Engineering Plastics* 6(3):196-207 (1993).
Coatings Additives: Silquest (R) A-178 Silane http://www.gesilicones.com/gesilicones/eu1/osi//grade/mastergrade_kit_one_part.jsp?masterGradeld=3001367&categoryId=3000016&ty . . . , 2003.

* cited by examiner

*Primary Examiner* — Tae H Yoon

(74) *Attorney, Agent, or Firm* — Ann M. Knab; Thad McMurray

(57) ABSTRACT

A filler which is surface-modified with a compound of the formula $[(PG)-R^1-Z]_n-SP-[Y-R^2-(AG)]_m$ is particularly suitable for use in dental materials, for the preparation of adhesives, coatings and composites.

29 Claims, 1 Drawing Sheet

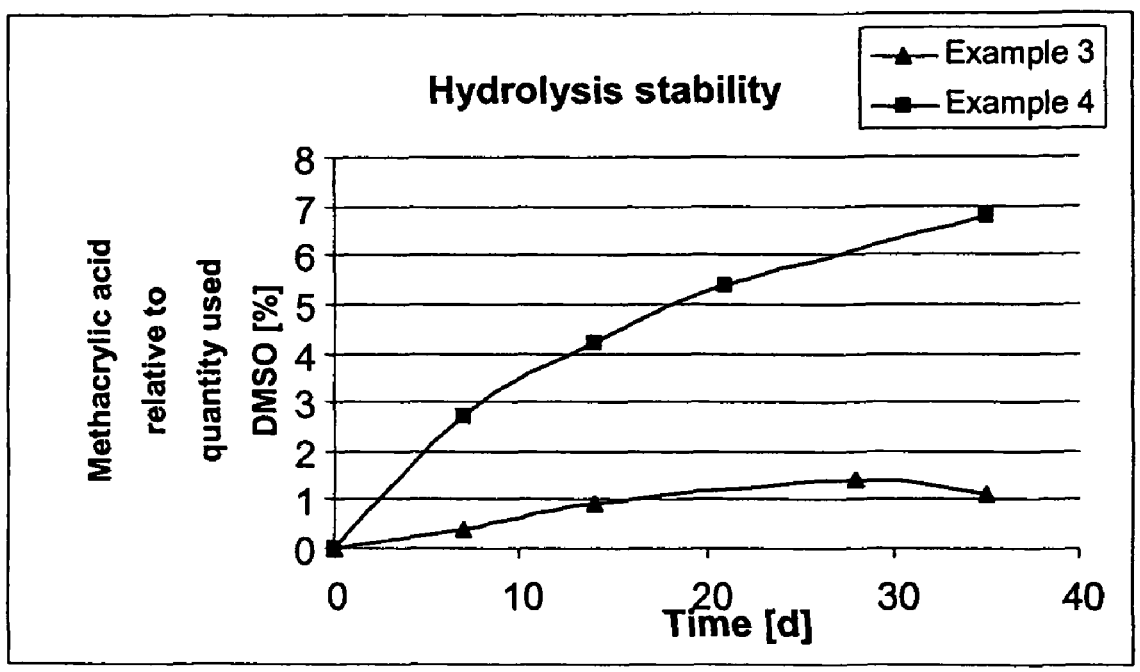

SURFACE-MODIFIED FILLERS

The present invention relates to surface-modified fillers which are particularly suitable for use in dental materials, for the preparation of adhesives, coatings and composites.

Filled materials based on (meth)acrylate monomers are used in restorative dentistry as filling and fixing materials fissure sealers, cements for orthodontology, as coating materials and as adhesives. The fillers used here can be divided into organic and inorganic fillers, inorganic fillers mostly being used. In turn these can be subdivided into oxidic and non-oxidic fillers. Oxidic fillers are then further classified as siliceous and non-siliceous fillers.

Siliceous fillers include for example ground glasses, such as e.g. barium silicate glasses (U.S. Pat. No. 4,220,582), strontium silicate glasses (DE 43 23 143) and X-ray-opaque aluminium-fluoro silicate glasses, which are used above all in (meth)acrylate-reinforced glass ionomers (U.S. Pat. No. 5,367,002, U.S. Pat. No. 5,871,360).

As a rule, to improve the mechanical properties the surfaces of the fillers are modified such that they are covalently bound into the polymer matrix by copolymerization during the curing of the material. With inorganic, siliceous fillers in most cases a silanization, i.e. a surface modification with pre-hydrolyzed (meth)acryloxyalkyltrialkoxysilanes, such as e.g. 3-methacryloxypropyltrimethoxysilane, is carried out. During silanization the formed silanol reacts with free Si—OH groups of the filler surface (cf. E. P. Plueddemann, "Silane Coupling Agents", Plenum Press, $2^{nd}$ Ed., New York and London, 1991).

GB 1 488 403 discloses lithium-aluminium-silicate glasses which are modified with trimethoxy-(3-methacryloyloxypropyl) silane.

DE 40 29 230 discloses filling and fixing materials based on mixed oxides e.g. zirconium oxide and silicon dioxide, which can be silanized with α-methacryloxypropyltrimethoxysilane.

Fissure sealers are known from US 2002/0072551 which contain various fillers, such as e.g. ground barium or lithium-aluminium silicate glass which is surface-treated with silanes such as γ-methacryloxypropyltrimethoxysilane, dimethyldichlorosilane or hexamethylenedisilazane.

US 2002/0065337 proposes silanes such as 3-methacryloxypropyltrimethoxysilane, 3-methacryloxypropyldimethoxymonochlorosilane and 3-methacryloxypropyldichloromonomethoxysilane etc. for the silanizing of nanoparticles based on ground glass, silicic acids, zeolites etc.

Glass ionomer fillers are known from US 2004/0010055 which are modified with a silane which contains a polyalkoxyethylene group.

DE 24 05 578 A1 discloses dental materials which contain as filler amorphous silicic acid with a maximum particle size of 0.07 μm. The filler is treated with trimethoxy-(3-methacryloyloxypropyl)silane.

Amorphous, spherical mixed oxides based on silicon and zirconium oxide are known from DE 32 47 800 A1 which are treated with γ-methacryloxypropyltrimethoxysilane and are suitable as a filler for restorative material.

DE 195 08 586 A1 discloses polymerizable dental materials which contain as fillers spherical particles based on $SiO_2$ and oxides of elements of groups I, II, III and IV of the periodic table. The filler particles can be coated with a layer made of a polymerizable organic binder. To modify the surface the particles are treated for example with trimethoxy or triethoxyvinylsilane. Such mixed oxides are used, in addition to their reinforcing effect, to increase X-ray opacity, to set the transparency and to adapt the refractive index.

Non-siliceous fillers based on zirconium oxide are known from WO 00/69392 which are surface-modified with organo-functional coupling agents such as hydrolyzable methacryloyloxyzirconates or methacryloyloxyaluminozirconates. Alternatively the coupling agents can be bound to the particle surface via phosphonate bonds. Moreover the particle can be further modified with silanes such as dimethylethoxyvinylsilane.

Surface-modified tantalum oxide is known from WO 98/13008 and yttrium oxide from DE 100 18 405. These fillers are particularly suitable as X-ray contrast media. On the other hand aluminium and titanium oxides frequently serve as opacifiers because of their high refractive index.

According to U.S. Pat. No. 6,387,981, non-siliceous fillers such as zirconium oxide can also be surface-conditioned by methacrylate-modified polyethercarboxylic acids.

Moreover, the surface modification of non-siliceous fillers with methacryloyloxyphosphates is known from U.S. Pat. No. 6,417,244.

A feature common to the above-described fillers is that adhesion promoters which are not stable under acid conditions are mostly used for surface modification. However, self-etching, self-conditioning restoration materials which are characterized by there being no need for preconditioning of the tooth hard substance, are being used ever more frequently in dentistry. These include self-etching dentine/enamel adhesives, methacrylate-reinforced glass ionomers, self-adhering composites or also compomers.

Self-etching dentine/enamel adhesives are mostly structured such that they contain an acid adhesive monomer, one or more non-acid comonomers, water or hydrous solvent mixtures, a polymerization initiator and optionally further additives.

U.S. Pat. No. 6,214,101 discloses self-etching methacrylate-reinforced glass ionomers which are present as a paste/paste system. One of the pastes is a water-based mixture which contains a polyacid, such as e.g. polyacrylic or polymaleic acid, and silane-modified barium glass powder.

If surface-modified fillers of the above-described type are incorporated into such self-etching systems the problem arises that the polymerizable groups of the adhesion promoters are split off by hydrolysis, so that a covalent binding of the filler into the polymer network is no longer possible. This impairs the reinforcing effect of the filler, and there is a clear reduction of the mechanical properties of the cured dental material if it is stored in water. The dental material loses its fitness for clinical use over time because of hydrolysis.

BRIEF DESCRIPTION OF THE DRAWING

FIG. 1 shows the results of hydrolysis-stability tests of OX50 silanized with 3-(methacrylamido)propyltrimethoxysilane (Example 3) and OX50 silanized with 3-(methacryloxy)propyltrimethoxysilane (Example 4, comparison).

The object of the invention is to provide fillers with radically polymerizable groups which are hydrolysis-stable vis-à-vis aqueous acids.

The object is achieved according to the invention by a filler which is surface-modified with a compound of the formula (I),

in which
AG is —P(=O)(OH)$_2$, —O—P(=O)(OH)$_2$, preferably —COOH, —SO$_2$OH, —SiR$^3$R$^4$X, or a chelating group,
R$^1$ is a C$_1$-C$_3$ alkylene group or cyclopropylene group or is absent,
R$^2$ is a C$_1$-C$_{10}$ alkylene group or is absent,
R$^3$ is a C$_1$-C$_8$ alkyl group, chlorine or OR$^5$,
R$^4$ is a C$_1$-C$_8$ alkyl group, phenyl, chlorine or OR$_5$,
R$^5$ is a C$_1$-C$_6$ alkyl group,
X is OR$^5$ or chlorine,
Y is O, S, CO—NH, O—CO—NH, NH—CO—NH or is absent, Y being absent if R$^2$ is absent,
Z is O, S, CO—NR$^6$, O—CO—NH, NH—CO—NH or is absent, R$^6$ being H or C$_1$-C$_6$ alkyl, PG is a radically polymerizable group of the formula

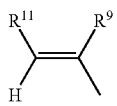

in which
R$^9$ is H, C$_1$-C$_3$ alkyl, C$_1$-C$_3$-hydroxyalkyl or COOR$^{10}$,
R$^{10}$ is H, C$_1$-C$_{10}$ alkyl, 1,6-dimethylphenyl or mesityl,
R$^{11}$ is H or phenyl,
m is 1 or 2,
n is 1, 2, 3 or 4,
SP is absent or an (n+m)-valent linear or branched aliphatic C$_1$-C$_{30}$ radical in which the carbon chain can be interrupted by O, S, CO—NH, O—CO—NH or NH—CO—NH, an (n+m)-valent aromatic C$_6$-C$_{18}$ radical, an (n+m)-valent cycloaliphatic C$_3$-C$_{18}$ radical or an (n+m)-valent heterocyclic C$_3$-C$_{18}$ radical, where the radicals can be substituted or unsubstituted,
in which, if AG is a silyl radical of the formula —SiR$^3$R$^4$X and PG a vinyl group of the formula H$_2$C═CH—, R$^1$ and Z are not absent simultaneously. In this case R$^1$ is a C$_1$-C$_3$ alkylene group or cyclopropylene group and/or Z is O, S, CO—NR$^6$, O—CO—NH, NH—CO—NH.

By the statement that a radical can be interrupted by foreign atoms or groups such as oxygen or sulphur is meant that one or more of the foreign atoms or one or more of the groups are integrated in a carbon chain. It follows that the foreign atoms or groups cannot be terminal, i.e. an attachment to neighbouring groups always takes place via a carbon atom, and that the number of foreign atoms and groups must necessarily be smaller than the number of carbon atoms.

Formula (I) extends only to compounds which are compatible with chemical valency theory.

The substituents optionally present in the radical SP are preferably selected from C$_1$-C$_5$ alkyl, Cl, Br and/or OH.

Preferred chelating groups are bidentate, tetradentate and hexadentate ligands. Preferred bidentate ligands are β-diketo groups of the formula —R$^7$—C(═O)—CH$_2$—C(═O)—R$^8$, in which R$^7$ is C$_1$-C$_3$ alkylene and R$^8$ C$_1$-C$_3$ alkyl, salicylic acid groups and salicylic aldehyde groups, glycinate, phenanthroline, bipyridyl and ethylenediamine. Particularly preferred bidentate ligands are the acetyl acetonate group and the salicylic acid group:

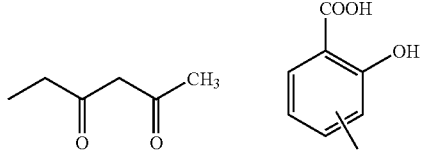

acetyl acetonate radical salicylic acid radical

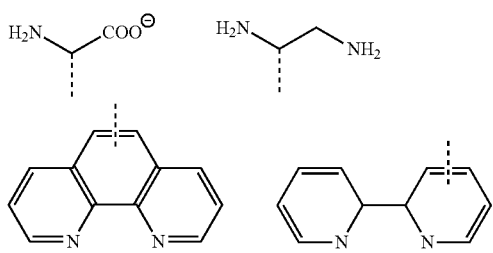

glycinate ethylenediamine phenanthroline bipyridyl

Preferred tridentate ligands are diethylenetriamine and iminodiacetate:

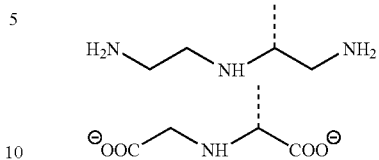

Preferred tetradentate ligands are tris(2-aminoethyl)amine and aminotriacetate:

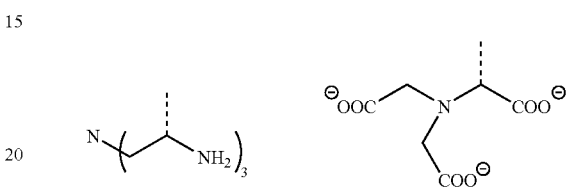

A preferred hexadentate ligand is ethylenediamine tetraacetate:

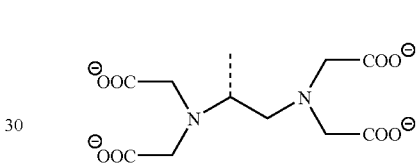

Acid groups and silane groups are preferred as adhesive groups.

PG is preferably a radically polymerizable group of the formula

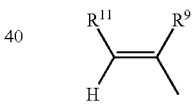

in which
R$^9$ is H, CH$_3$, C$_2$H$_5$, hydroxymethyl, hydroxyethyl or COOR$^{10}$,
R$^{10}$ is H, C$_1$-C$_3$ alkyl, 1,6-dimethylphenyl or mesityl,
R$^{11}$ is H or phenyl.

Preferred polymerizable groups PG are vinyl groups of the formula H$_2$C═C(—R$^9$)—, acrylic acid groups of the formula H$_2$C═C (—COOR$^{10}$)—, allyl, styryl and/or vinylcyclopropyl.

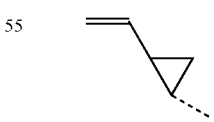

vinylcyclopropyl

Preferred definitions of the above variables, which can be chosen independently of each other, are:
AG=—P(═O)(OH)$_2$, —O—P (═O)(OH)$_2$ and in particular —COOH or —SiR$^3$R$^4$X,
R$^1$=a methylene group, cyclopropylene group or is absent,
R$^2$=a C$_1$-C$_3$ alkylene group or is absent,
R$^3$=a C$_1$-C$_3$ alkyl group, chlorine, in particular OR$^5$, $R^4$=a $C_1$-$C_3$ alkyl group, phenyl, chlorine, in particular $OR^5$, $R^5$=a $C_1$-$C_2$ alkyl group, $R^6$=H, a $C_1$-$C_3$ alkyl group, in particular methyl, X=chlorine, in particular $OR^5$, Z=CO—$NR^6$ or is absent, Y=is absent, PG=for Z=is absent: a vinyl group $H_2C$=C(—$R^9$)— in which $R^9$ is H, $CH_3$, $C_2H_5$, hydroxymethyl or hydroxyethyl, or an acrylic acid group $H_2C$=C(—$COOR^{10}$)— in which $R^{10}$ is H, $C_1$-$C_3$ alkyl, 1,6-dimethylphenyl or mesityl, for Z=CO—$NR^6$: a vinyl group $H_2C$=C(—$R^9$)— in which $R^9$ is H or $CH_3$, m=1 or 2, n=1 or 2, SP=is absent or an (n+m)-valent linear or branched aliphatic $C_1$-$C_6$ radical, an (n+m)-valent aromatic $C_6$-$C_{10}$ radical, an (n+m)-valent cycloaliphatic $C_3$-$C_{10}$ radical or an (n+m)-valent heterocyclic $C_3$-$C_{10}$ radical, where the radicals can be substituted or unsubstituted, in which, if AG is a silyl radical of the formula —$SiR^3R^4X$ and PG a vinyl group of the formula $H_2C$=CH—, $R^1$ is a methylene group or cyclopropylene group and/or Z CO—$NR^6$.

Quite particularly preferred are compounds in which at least two and in particular all variables have one of the preferred meanings.

The compounds of the general formula (I) used according to the invention as adhesion promoters are in some cases known and in some cases even commercially available.

Preferred compounds of the formula (I) in which AG is a carboxyl group (carboxylic acids) are α-hydroxymethylacrylic acid, α,Ω-(meth)acrylamidoalkylenecarboxylic acids, (meth)acrylamidoarylenecarboxylic acids, such as e.g. 3-(methacryloylamino)-propionic acid, 3-(acryloylamino)-propionic acid, 6-(methacryloylamino)-caproic acid, 8-(methacryloylamino)-caprylic acid, 4-(methacryloylamino)-benzoic acid or 4-(acryloylamino)-benzoic acid:

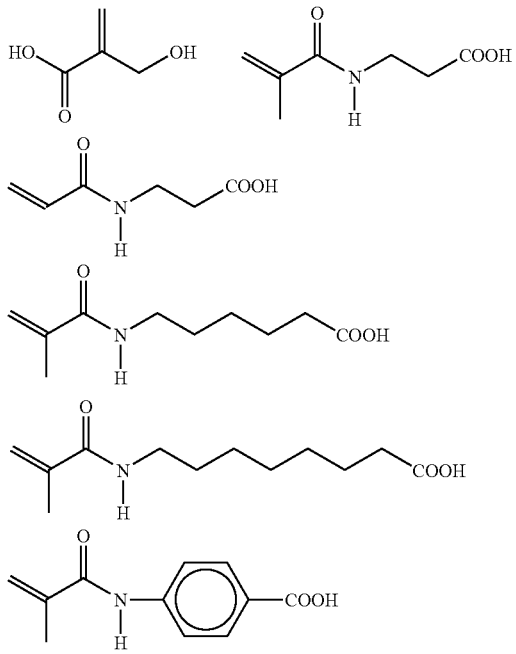

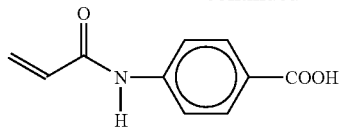

Preferred compounds of the formula (I) in which AG is a phosphonic acid group —P(=O)(OH)$_2$ (phosphonic acids) are vinyl phosphonic acid, 4-vinyl benzyl phosphonic acid, and the acrylate ether phosphonic acids disclosed in EP 909 761 B1 and DE 102 34 326 B3, in particular 2-[4-(dihydroxyphosphoryl)-2-oxa-butyl]-ethyl acrylate, 2-[4-(dihydroxyphosphoryl)-2-oxa-butyl]-acrylic acid and 2-[4-(dihydroxyphosphoryl)-2-oxa-butyl]-acrylic acid-2,4,6-trimethylphenylester. Further preferred are (meth)acrylamidoalkylenephosphonic acids and bisphosphonic acids, in particular 2-acrylamido- and 2-methacrylamido-2-methylpropanephosphonic acid (DE 32 10 775), the phosphonic acid compounds disclosed in DE 33 13 819, JP PS 62 63,314 and Chem. Abstr. 107 (1987), 41318f, in particular methacrylic acid-(2-phosphono-1,1-dimethylethylamine) and the N-acrylaminomethane bisphosphonic acids described in DD 273 846 A1:

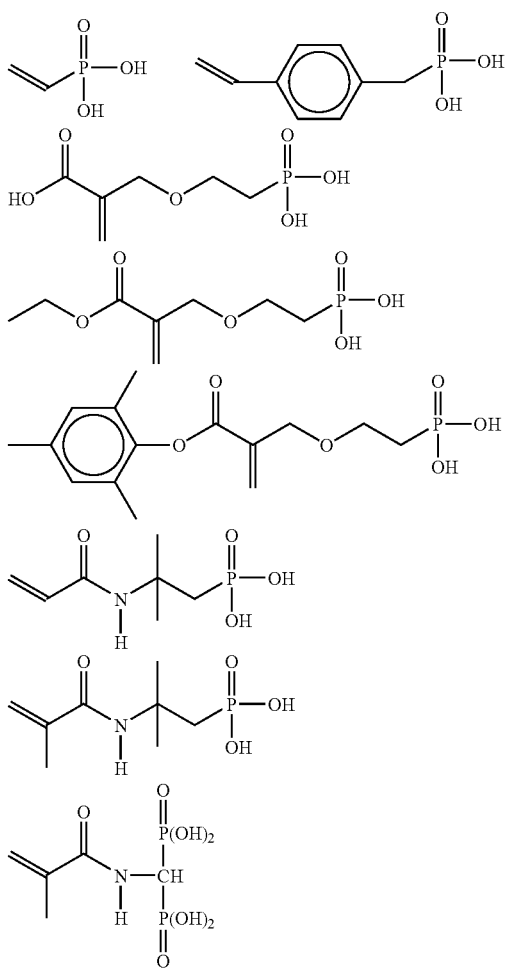

Preferred compounds of the formula (I) in which AG is a phosphoric acid group —O—P(=O)(OH)$_2$ (dihydrogen phosphate) are acrylic ether phosphates, in particular 2-[4-(dihydroxyphosphoryloxy)-2-oxa-butyl]-acrylic acid and 2-[4-(dihydroxyphosphoryloxy)-2-oxa-butyl]-acrylic acid-2,4,6-trimethylphenylester, (meth)acrylamidoalkylene-, cycloalkylene- and arylene dihydrogen phosphate, in particular 2-(N-acryloylamino)ethyl dihydrogen phosphate, 2-(N-methacryloylamino)ethyl dihydrogen phosphate, 6-(N-acryloylamino)hexyl dihydrogen phosphate, 6-(N-methacryloylamino)hexyl dihydrogen phosphate, 4-(N-acryloylamino)phenyl dihydrogen phosphate, 4-(N-methacryloylamino)phenyl dihydrogen phosphate, 1,3-bis-(N-acryloylamino)-propan-2-yl-dihydrogen phosphate, 1,3-bis-(N-methacryloylamino)-propan-2-yl-dihydrogen phosphate, 1,3-bis-(N-acryloyl-N-methyl-amino)-propan-2-yl-dihydrogen phosphate and 1,3-bis-(N-acryloyl-N-ethyl-amino)-propan-2-yl-dihydrogen phosphate:

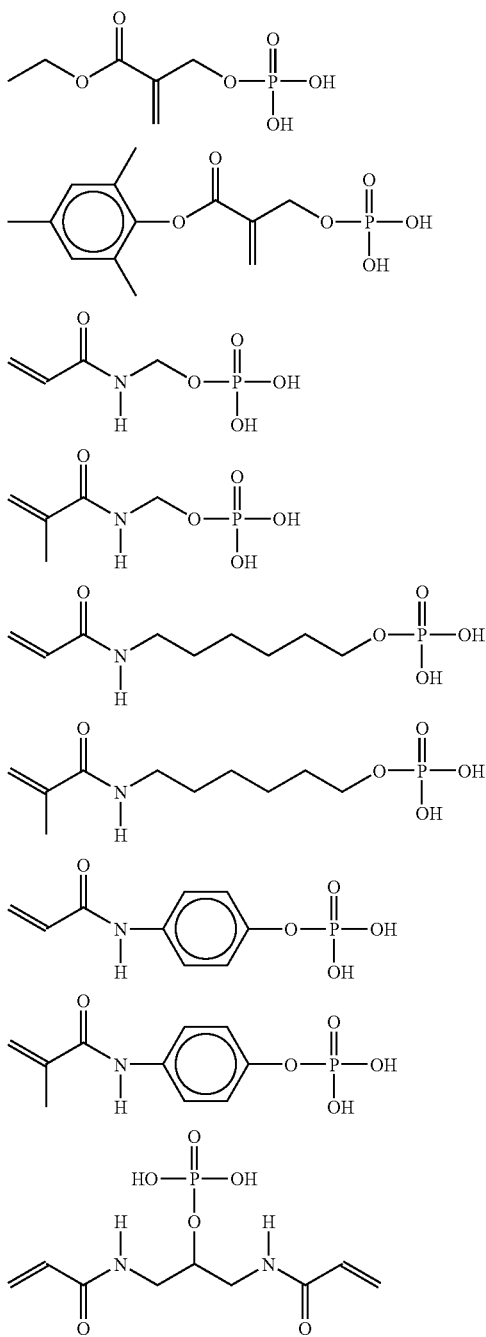

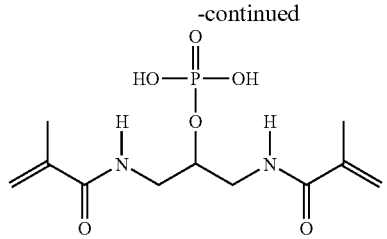

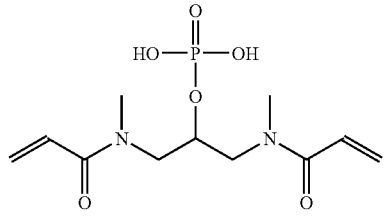

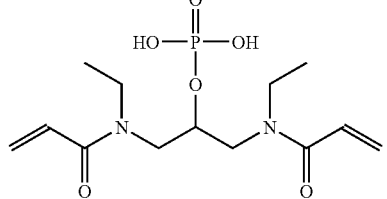

Preferred compounds of the formula (I) in which AG is a sulphonic acid group —SO$_2$OH (sulphonic acids) are vinyl sulphonic acid, 4-vinylphenyl sulphonic acid and 2-acryloylamino-2-methylpropane sulphonic acid:

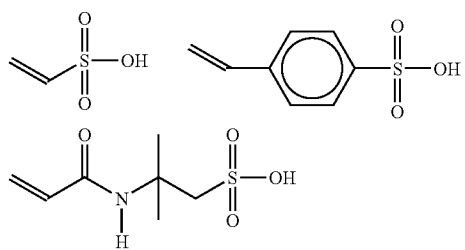

Preferred compounds of the formula (I) in which AG is a silyl group —SiR$^3$R$^4$X (silane), are (meth)acrylamidoalkyl-trialkoxysilane, in particular 3-(N-methacryloylamino)-propyltrimethoxysilane, 3-(N-acryloylamino)-propyltrimethoxysilane, 3-(N-methacryloylamino)-propyltriethoxysilane, 3-(N-methacryl-N-ethyl-amino)-propyltrimethoxysilane, 3-(N-methacryl-N-ethyl-amino)-propyltrimethoxysilane, 3-(N-acryl-N-ethylamino)-propyltrimethoxysilane, 3-(N-methacryl-N-methyl-amino)-propyltrimethoxysilane, 3-(N-acryl-N-methylamino)-propyltrimethoxysilane:

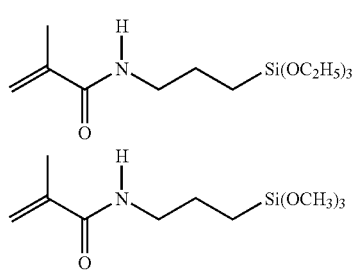

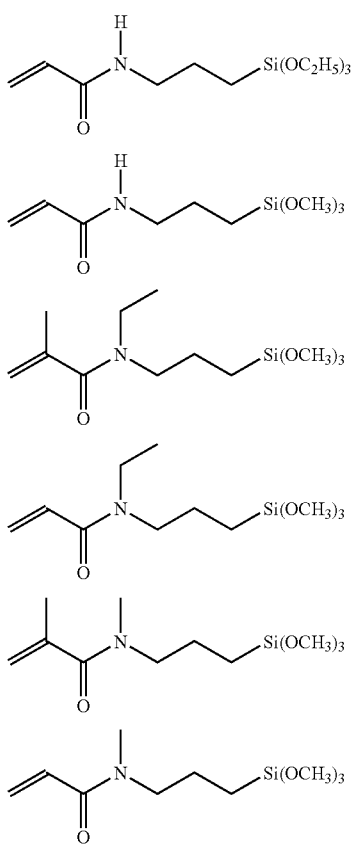

Further preferred are (meth)acrylamidoalkyl-alkyl and aryldialkoxysilanes or (meth)acrylamidoalkyltrichlorosilanes, in particular 3-(N-methacryloylamino)-propylmethyldimethoxysilane, 3-(N-acryloylamino)-propylmethyldimethoxysilane, 3-(N-methacryloylamino)-propylphenyldimethoxysilane, 3-(N-acryloylamino)-propylphenyldimethoxysilane, 3-(N-methacryl-N-ethylamino)-propyl-methyldimethoxysilane, 3-(N-Acryl-N-ethylamino)-propyl-methyldimethoxysilane, 3-(N-methacryl-N-methyl-amino)-propyltrichlorosilane and 3-(N-acryl-N-methylamino)-propyltrichlorosilane:

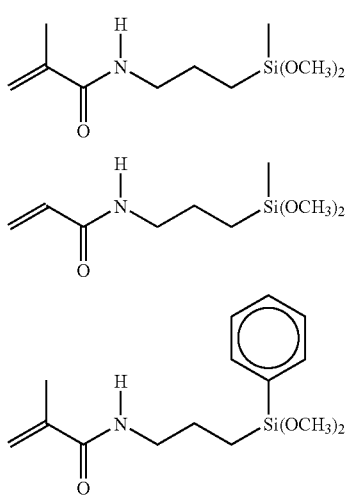

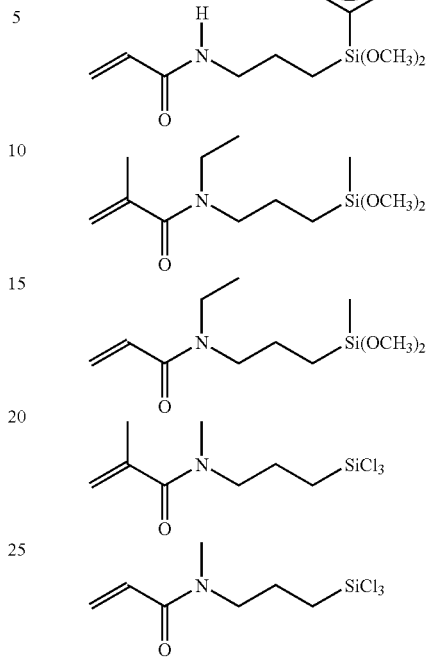

Preferred compounds of the formula (I) in which AG is a chelating group are methacryloylacetone (cf. P. Teyssie, G. Smets, Makromol. Chem. 26 (1958) 245), 4-vinylbenzoyl acetone (A. Mansri, P. F. Casals, A. Oulmidi, K. Guemra, D. Reyx, Eur. Polym. J. 32 (1996) 269) or 4-methacryloylaminosalicylic acid:

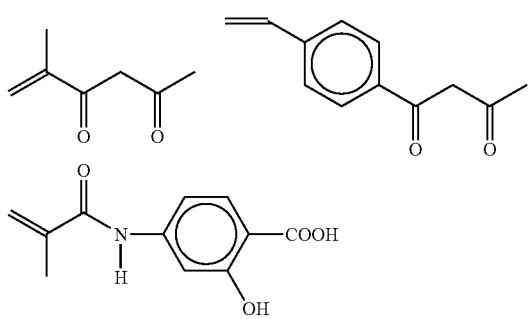

Surface modification of the fillers with the adhesion promoters of the formula (I) according to the invention can take place in various ways.

Liquid adhesion promoters are preferably mixed direct with the fillers, then the fillers are dried to remove condensation products.

To achieve a better wetting of the filler surface it is advantageous, in particular with very fine-particled fillers with a specific surface area of more than 20 or 40 m$^2$/g, to disperse the filler in a solution of the adhesion promoter in a suitable solvent. The adsorption of the adhesion promoter by the filler surface can be influenced through the polarity of the solvent. Preferred solvents are cyclohexane, THF, dioxane, ethanol and water. The degree of surface modification depends inter alia on the quantity of filler and the specific surface area of the filler, on the quantity of adhesion promoter, on the reaction time, on the temperature and on the filler pretreatment, such as e.g. on a predrying.

The various influencing factors are very well examined, in particular in the case of the silanization of fillers (cf. E. P. Plueddemann, "Silane Coupling Agents", Plenum Press, 2$^{nd}$ Ed., New York and London, 1991; A. Guillet, Macromol. Symp. 194 (2003) 63). In the case of silanes, surface modification takes place through hydrolysis of the hydrolyzable groups at the silicon atom by adding water followed by condensation e.g. with hydroxyl groups on the surface of the filler. In the case of $SiO_2$ or siliceous fillers siloxane bonds form between silanol groups of the filler particles and alkoxysilyl groups of the silane adhesion promoters. The hydrolyzable groups can also react directly with the silanol groups of the particle surface with formation of a siloxane bond. In the last case the addition of water is not required. The residual water at the filler surface often also suffices. The reaction is then preferably carried out in non-polar solvents. The pH influences the hydrolysis and the condensation. Therefore as a rule an acid or basic catalyst is added. The acid or basic group can however already be included as an organic radical in the silane or be released during hydrolysis. The suspension can be heated in order to accelerate the reaction with the surface. The condensation can be further forced through a following evaporation of the solvent and drying of the filler. Optionally siloxane species not bound to the surface can be washed off in a following washing process.

When using acids and chelates for surface modification these are preferably stirred for several hours at room temperature or higher temperature together with the dispersed filler in a suitable solvent in which the acid or the chelate ligand are soluble. The solvent is then evaporated and the filler dried. Alternatively the filler can be separated off directly, washed and then dried.

Through chemical reaction of the adhesive groups of the adhesion promoter, e.g. of the acid or chelating groups with suitable reactive centres of the filler surface, such as e.g. OH groups in the case of oxidic fillers, such as $TiO_2$ or $Al_2O_3$, or metal ions of corresponding transition metal compounds, e.g. $Zr^{4+}$ ions in the case of $ZrO_2$ or $Yb^{3+}$ ions in the case of ytterbium fluoride, there is a strong covalent, ionic or coordination-chemical attachment of the adhesion promoter to the filler surface.

After the conclusion of the reaction between filler and adhesion promoter the filler is separated off, optionally washed with the same or another solvent, subjected to an optional heat treatment, optionally washed once again and then dried. In the case of fillers which have a tendency to agglomerate it may be necessary to grind these after the surface modification or pulverize them in some other way.

Preferred fillers according to the invention are those which are based on inorganic particulate fillers with an average particle size of 0.01 to 5 μm. These are obtained by treating untreated inorganic particulate fillers with one or more compounds of the formula (I) in the way described above. By untreated fillers is meant fillers which have not yet been modified with compounds of the formula (I). Below these are also called starting materials or starting fillers.

Preferred starting materials for the preparation of the fillers according to the invention are an amorphous filler based on one or more metal oxides and/or silicon oxide, particularly preferably untreated fillers based on $ZrO_2$, $Ta_2O_5$, $TiO_2$, mixed oxides of $SiO_2$, $ZrO_2$ and/or $TiO_2$, $Yb_2O_3$, $Y_2O_3$, $YbF_3$, $Al_2O_3$ and AlO(OH), boehmite, pyrogenic silica or precipitated silica.

Moreover quartz, glass ceramic or glass powders, preferably with an average particle size of 0.01 to 5 μm, and X-ray-opaque metal compounds such as ytterbium trifluoride are preferred as starting fillers. Unless stated otherwise the average particle size is always the average by weight which is preferably established by light scattering.

The starting fillers preferably have a specific surface area of more than 20 m$^2$/g and in particular more than 40 m$^2$/g, fillers with a maximum specific surface area of 300 m$^2$/g being particularly preferred.

Fillers with no, or only a small, $SiO_2$ content are preferably treated with compounds of the formula (I) in which AG is —P(=O)(OH)$_2$ or —O—P(=O)(OH)$_2$. By a small $SiO_2$ content is meant a $SiO_2$ content of less than 25 wt.-% and in particular less than 10 wt.-% relative to the mass of the filler in question with a uniform distribution of the $SiO_2$ in the filler. If the $SiO_2$ accumulates in the surface area of the filler the given concentrations fall correspondingly.

The fillers modified according to the invention with a compound of the formula (I) are particularly suitable for the preparation of dental materials. For the preparation of dental materials, the fillers modified with compounds of the formula (I) are mixed with a radically polymerizable binder and optionally an initiator for the radical polymerization.

Preferred binders are hydrolysis-stable diluting monomers, such as hydrolysis-stable mono(meth)acrylates, e.g. mesityl methacrylate, N-mono- or N,N-disubstituted acrylamides, such as e.g. N-ethylacrylamide, N,N-dimethacrylamide, N-(2-hydroxyethyl)acrylamide and N-methyl-N-(2-hydroxyethyl)acrylamide, N-monosubstituted methacrylamides, such as e.g. N-ethylmethacrylamide and N-(2-hydroxyethyl)methacrylamide, and N-vinylpyrrolidone.

In the context of the present invention, by diluting monomers is meant liquid monomers with one or more polymerizable groups which are characterized by a viscosity η of less than 100 mPa·s (measured at 20° C.).

Monomers which are stable in water or in mixtures of water and water-miscible solvents at a concentration of approx. 20 wt.-% and a pH of approx. 2.0 at 37° C. for at least 6 weeks, i.e. which hydrolyze by less than 5%, are described as hydrolysis-stable.

Additionally, hydrolysis-stable cross-linking monomers are preferred as binders. By cross-linking monomers is meant monomers with two or more, preferably 2 to 4 radically polymerizable groups. Preferred cross-linking monomers are cross-linking pyrrolidones, such as e.g. 1,6-bis(3-vinyl-2-pyrrolidonyl)-hexane, or commercially available bisacrylamides, such as methylene or ethylenebisacrylamide, bis(meth)acrylamides, such as e.g. N,N'-diethyl-1,3-bis(acrylamido)-propane, 1,3-bis(methacrylamido)-propane, 1,4-bis(methacrylamido)-butane, 1,4-bis(acrylamido)-butane and 1,4-bis(acrylamido)-piperazine, which can be synthesized by reaction from the corresponding diamines with (meth)acrylic acid chloride. The cross-linking monomers can be used alone or together with one or more diluting monomers as binders.

According to a particularly preferred version the binder contains at least one acid monomer, also called adhesive monomer below. These are monomers which contain at least one acid group, particularly preferably 1 to 4 acid groups. Preferred acid groups are carboxylic acid, sulphonic acid, phosphonic acid and/or phosphoric acid groups. Compounds which contain carboxylic acid, phosphonic acid and/or phosphoric acid groups as acid group are particularly preferred. Compounds with more than one acid group can contain different acid groups or preferably identical acid groups.

Particularly suitable as adhesive monomers for enamel/dentine adhesives or self-adhering composites are the above-described hydrolysis-stable polymerizable acrylateetherphosphonic acids such as e.g. 2-[4-(dihydroxyphosphoryl)-2-oxa-butyl]-acrylic acid ethyl ester, 2-[4-(dihydroxyphosphoryl)-2-oxa-butyl]-acrylic acid and 2-[4-(dihydroxyphosphoryl)-2-oxa-butyl]-acrylic acid-2,4,6-trimethylphenylester, (meth)acrylamidoalkylenephosphonic acids or -bisphosphonic acids such as e.g. acrylic acid-(2-phosphono-1,1-dimethylethylamine) or methacrylic acid-(2- phosphono-1,1-dimethylethylamine) or N-acrylaminomethanebisphosphonic acid.

Also particularly well suited as adhesive monomers are hydrolysis-stable, polymerizable dihydrogen phosphates such as (meth)acrylamidoalkylene, cycloalkylene or arylenedihydrogen phosphates, e.g. 2-(N-acryloylamino)ethyldihydrogen phosphate, 2-(N-methacryloylamino)ethyldihydrogen phosphate, 6-(N-acryloylamino)hexyldihydrogen phosphate, 6-(N-methacryloylamino)hexyldihydrogen phosphate, 4-(N-acryloylamino)phenyldihydrogen phosphate, 4-(N-methacryloylamino)phenyldihydrogen phosphate, 1,3-bis-(N-acryloylamino)-propan-2-yl-dihydrogen phosphate, 1,3-bis-(N-methacryloylamino)-propan-2-yl-dihydrogen phosphate, 1,3-bis-(N-acryloyl-N-methyl-amino)-propan-2-yl-dihydrogen phosphate or 1,3-bis-(N-acryloyl-N-ethyl-amino)-propan-2-yl dihydrogen phosphate.

Particularly useful adhesive monomers are above all 2-[4-(dihydroxyphosphoryl)-2-oxa-butyl]-acrylic acid ethyl ester, 2-[4-(dihydroxyphosphoryl)-2-oxa-butyl]-acrylic acid, 2-[4-(dihydroxyphosphoryl)-2-oxa-butyl]-acrylic acid-2,4,6-trimethylphenylester, 6-(N-acryloylamino)hexyldihydrogen phosphate, 6-(N-methacryloylamino)hexyldihydrogen phosphate, 1,3-bis-(N-acryloylamino)-propan-2-yl-dihydrogen phosphate, 1,3-bis-(N-methacryloylamino)-propan-2-yl-dihydrogen phosphate.

The acid monomers are a constituent of the binder, and unlike the substances used for the surface modification of the fillers, can move freely therein. The compounds bound to the filler surface no longer have adhesion-promoting properties.

Single monomers or mixtures of two or more monomers can be used as binders. Preferably the binder contains at least one cross-linking monomer; binders which contain exclusively cross-linking monomers are particularly preferred. According to a particularly preferred version the binder contains at least one acid monomer.

Filler and binder are mixed with each other optionally with the addition of one or more solvents, with acetone, isopropanol and ethanol being preferred as solvents. The initiator and further additives are then optionally added.

The dental materials according to the invention can be cured by radical polymerization. Depending on the choice of initiator, curing can take place by photochemical or redox-induced radical polymerization.

Examples of preferred photoinitiators are benzophenone, benzoin and its derivatives or α-diketones or their derivatives such as 9,10-phenanthrenequinone, diacetyl or 4,4-dichlorobenzil. It is preferred to use camphorquinone and 2,2-dimethoxy-2-phenyl-acetophenone and more preferably α-diketones in combination with amines as reducing agent, such as e.g. 4-(N,N-dimethylamino)-benzoic acid ester, N,N-dimethylaminoethylmethacrylate, N,N-dimethyl-sym.-xylidine or triethanolamine. Moreover, acylphosphines, such as e.g. 2,4,6-trimethylbenzoyldiphenyl or bis(2,6-dichlorobenzoyl)-4-N-propylphenylphosphinic oxide are also particularly suitable.

Redox-initiator combinations, preferably combinations of benzoylperoxide with N,N-dimethylsym.-xylidine or N,N-dimethyl-p-toluidine, are used as initiators for a polymerization carried out at room temperature. Moreover, redox systems consisting of peroxides and such reducing agents, such as e.g. ascorbic acid, barbiturates or sulphinic acids, are particularly suitable.

Dental materials which contain the following components are particularly preferred:
(a) 5 to 90 wt.-%, in particular 5 to 50 wt.-% filler which is surface-modified with adhesion promoter of the formula (I);
(b) 9.9 to 90 wt.-%, in particular 0 to 40 wt.-%, radically polymerizable monomer (binder);
(c) 0.1 to 5.0 wt.-%, in particular 0.2 to 2.0 wt.-%, initiator for the radical polymerization, and/or
(d) 0 to 70 wt.-%, in particular 0 to 50 wt.-%, solvent.

All percentages are relative, unless otherwise stated, to the total mass of the dental material.

The dental material can contain one or more fillers which are modified with a compound of the formula (I). It is however preferred that all filler components of the dental material are modified in the given way.

Acid monomers are preferably used in a quantity of 0 to 70 wt.-%, particularly preferably 0 to 50 wt.-% and quite particularly preferably 3 to 30 wt.-%, relative to the total mass of the material.

The dental materials are particularly suitable as adhesives, filling composites, fixing cements, fissure sealers or coating materials.

The invention is described in more detail below with the help of examples.

EXAMPLES

Example 1

Synthesis of
3-(methacrylamido)propyltrimethoxysilane 77.4 g 3-(amino)propyltrimethoxysilane, 43.7 g triethylamine and 25 mg di-tert.-butyl-p-cresol were dissolved under argon in 500 ml dichloromethane. 45.1 g methacryloyl chloride was slowly added dropwise at −5° C. within 1 h, and the whole was then stirred for 1 h at 0° C. The precipitated hydrochloride was filtered off and washed with dichloromethane. The volatile constituents were removed at 40° C. under reduced pressure using the rotary evaporator. A yellow liquid with precipitated solid (hydrochloride) remained. The precipitation of the hydrochloride was completed by adding 150 ml diethyl ether, the precipitate was filtered off and the filtrate concentrated at 40° C. using a rotary evaporator with introduction of dry air. The brownish liquid was freed of residual volatile constituents at $4\times10^{-2}$ mbar, and the raw product (104.2 g) was distilled at a pressure of $6\times10^{-4}$ mbar. The product had a boiling point of 123-125° C. 76.4 g of product was obtained as yellowish, clear liquid.

Example 2

Synthesis of
3-((N-methyl)methacrylamido)propyltrimethoxysilane

The synthesis was carried out analogously to Example 1. 83.4 g 3-((N-methyl)amino)propyltrimethoxysilane was used instead of 3-(amino)propyltrimethoxysilane. The raw product, 102.2 g of a yellow, clear liquid, was distilled at a pressure of $6\times10^{-4}$ mbar with a boiling point of 118° C. 87.8 g of product was obtained as a colourless, clear liquid.

Example 3

Silanization of OX50 with
3-(methacrylamido)propyltrimethoxysilane 30 g pyrogenic silica with a particle size of 50 nm (OX 50, Degussa) was suspended in 300 g cyclohexane. After adding 3.86 g 3-(methacrylamido)propyltrimethoxysilane and 1.38 g propylamine, the whole was heated for 30 h to 70° C. The volatile constituents were removed using a rotary evaporator and the product was dried for 3 d at 50° C. Excess silane/condensate which was not bound on the particle surface was washed out by repeated dispersal and subsequent centrifuging in acetone, ethanol and then cyclohexane. The silanized powder was dried using the rotary evaporator. A white powder was obtained.

Example 4

Silanization of OX50 with 3-(methacryloxy)propyltrimethoxysilane (comparison example)

The process was the same as in Example 3. 3.87 g 3-(methacryloxy)propyltrimethoxysilane was used instead of 3.86 g 3-(methacrylamido)propyltrimethoxysilane. A white powder was obtained.

Example 5

Hydrolysis-Stability Test of the Silanized OX50

0.5 g of the silanized OX50 (from each of Example 3 or Comparison Example 4) was suspended in 2 g 1 N deuterium chloride solution in deuterium oxide, 0.019 g dimethyl sulphoxide being added as a reference in each case. 5 samples were prepared in separate flasks for each material. The suspensions were stirred intensively for approx. 1 h and then stored, well sealed, at 42° C. until NMR analysis. The samples were filtered over glass wool prior to spectroscopic examination. The clear solutions were each examined by means of $^1$H-NMR spectroscopy.

The first sample was examined after 2 h, the $2^{nd}$ sample after 1 week, the 3rd sample after 3 weeks, the $4^{th}$ sample after 4 weeks and the $5^{th}$ sample after 6 weeks. For this, the increase in the integral of the proton of the methacrylic acid group at 5.3 ppm relative to the integral of the protons of the phenol (MEHQ) at 6.1-6.0 ppm was observed. The increase in concentration of methacrylic acid, the hydrolysis product of the silane, was able to be estimated from this. The results are summarized in Table 1 and shown in a graph in FIG. 1. The filler treated according to the invention recognizably has a better hydrolysis stability under acid conditions (pH<2).

TABLE 1

Hydrolysis stability of silanized silicic acids

| Sample | Time | NMR (mol % methacrylic acid relative to the quantity of DMSO used) |
|---|---|---|
| Example 4 | 0 d | 0% |
| (comparison) | 7 d | 2.7% |
| | 14 d | 4.2% |
| | 21 d | 5.4% |
| | 35 d | 6.8% |
| Example 3 | 0 d | 0% |
| | 7 d | 0.4% |
| | 14 d | 0.9% |
| | 28 d | 1.4% |
| | 35 d | 1.1% |

The invention claimed is:

1. Dental material comprising
   (a) 5 to 90 wt.-% filler that is based on an inorganic filler and that is surface-modified with a compound of the formula (I), $$[(PG)\text{-}R^1\text{---}Z]_n\text{---}SP\text{---}[\text{---}R^2\text{-}(AG)]_m \quad (I)$$

in which
   AG is —SiR$^3$R$^4$X,
   R$^1$ is a C$_1$-C$_3$ alkylene group or cyclopropylene group or is absent,
   R$^2$ is a C$_1$-C$_{10}$ alkylene group or is absent,
   R$^3$ is a C$_1$-C$_8$ alkyl group, chlorine or OR$^5$,
   R$^4$ is a C$_1$-C$_8$ alkyl group, phenyl, chlorine or OR$^5$,
   R$^5$ is a C$_1$-C$_6$ alkyl group,
   X is OR$^5$ or chlorine,
   Z is CO—NR$^6$, in which R$^6$ is H or C$_1$-C$_6$ alkyl,
   PG is an allyl group, a styryl group, a vinyl cyclopropyl group or a radically polymerizable group of the formula

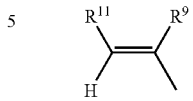

in which
   R$^9$ is H, C$_1$-C$_3$ alkyl, C$_1$-C$_3$ hydroxyalkyl or COOR$^{10}$,
   R$^{10}$ is H, C$_1$-C$_{10}$ alkyl, 1,6-dimethylphenyl or mesityl,
   R$^{11}$ is H or phenyl,
   m is 1 or 2,
   n is 1, 2, 3 or 4,
   SP is absent or an (n+m)-valent linear or branched aliphatic C$_1$-C$_{30}$ radical in which the carbon chain can be interrupted by O, S, CO—NH, O—CO—NH or NH—CO—NH, an (n+m)-valent aromatic C$_6$-C$_{18}$ radical, an (n+m)-valent cycloaliphatic C$_3$-C$_{18}$ radical or an (n+m)-valent heterocyclic C$_3$-C$_{18}$ radical, wherein the radicals can be substituted with a C$_1$-C$_5$ alkyl, Cl, Br and/or OH or unsubstituted,
   (b) 9.9 to 90 wt.-% radically polymerizable monomer,
   (c) 0.1 to 5.0 wt.-% initiator for the radical polymerization, and
   (d) 0 to 70 wt.-% solvent,
   each relative to the total mass of the dental material.

2. Dental material according to claim 1, in which PG is a vinyl group of the formula H$_2$C=C(—R$^9$)—, an acrylic acid group of the formula H$_2$C=C(—COOR$^{10}$)—, an allyl, a styryl and/or a vinyl cyclopropyl.

3. Dental material according to claim 1, in which at least one of the variables has one of the following meanings:
   R$^1$ is a methylene group, cyclopropylene group or is absent,
   R$^2$ is a C$_1$-C$_3$ alkylene group or is absent,
   R$^3$ is a C$_1$-C$_3$ alkyl group, chlorine or OR$^5$,
   R$^4$ is a C$_1$-C$_3$ alkyl group, phenyl, chlorine or OR$^5$,
   R$^5$ is a C$_1$-C$_2$ alkyl group,
   X is OR$^5$ or chlorine,
   PG is a vinyl group H$_2$C=C(—R$^9$)— in which R$^9$ is H or CH$_3$,
   m is 1 or 2,
   n is 1 or 2,
   SP is absent or an (n+m)-valent linear or branched aliphatic C$_1$-C$_6$ radical, an (n+m)-valent aromatic C$_6$-C$_{10}$ radical, an (n+m)-valent cycloaliphatic C$_3$-C$_{10}$ radical or an (n+m)-valent heterocyclic C$_3$-C$_{10}$ radical.

4. Dental material according to claim 1, wherein the filler is based on an inorganic, particulate filler with a particle size of 0.01 to 5 μm.

5. Dental material according to claim 4, wherein the filler is an amorphous filler based on one or more metal oxides and/or silicon oxide.

6. Dental material according to claim 4, wherein the filler is based on quartz, glass ceramic or glass powder.

7. Dental material according to claim 1, wherein the filler is based on an inorganic, particulate filler with a specific surface area of more than 20 m$^2$/g.

8. Dental material according to claim 1, wherein the filler is obtained by chemically reacting an inorganic particulate filler with a compound of the formula (I).

9. Dental material according to claim 1, which contains at least one acidic monomer.

10. Dental material according to claim 4, wherein the filler is based on ytterbium trifluoride.

11. Dental material according to claim 7, wherein the surface area is more than 40 m$^2$/g.

12. Dental material according to claim 1,
wherein
AG is —SiR$^3$R$^4$X,
R$^1$ is a methylene group or cyclopropylene group,
R$^2$ is a C$_1$-C$_{10}$ alkylene group or is absent,
R$^3$ is a C$_1$-C$_8$ alkyl group, chlorine or OR$^5$,
R$^4$ is a C$_1$-C$_8$ alkyl group, phenyl, chlorine or OR$^5$,
R$^5$ is a C$_1$-C$_6$ alkyl group,
X is OR$^5$ or chlorine,
Z is CO—NR$^6$, in which R$^6$ is H or C$_1$-C$_6$ alkyl,
PG is a vinyl group of the formula H$_2$C=CH—,
m is 1 or 2,
n is 1, 2, 3 or 4,
SP is absent or an (n+m)-valent linear or branched aliphatic C$_1$-C$_{30}$ radical in which the carbon chain can be interrupted by O, S, CO—NH, O—CO—NH or NH—CO—NH, an (n+m)-valent aromatic C$_6$-C$_{18}$ radical, an (n+m)-valent cycloaliphatic C$_3$-C$_{18}$ radical or an (n+m)-valent heterocyclic C$_3$-C$_{18}$ radical.

13. Dental material according to claim 1,
wherein
AG is —SiR$^3$R$^4$X,
R$^1$ is a methylene group, cyclopropylene group, or is absent,
R$^2$ is a C$_1$-C$_{10}$ alkylene group or is absent,
R$^3$ is a C$_1$-C$_8$ alkyl group, chlorine or OR$^5$,
R$^4$ is a C$_1$-C$_8$ alkyl group, phenyl, chlorine or OR$^5$,
R$^5$ is a C$_1$-C$_6$ alkyl group,
X is OR$^5$ or chlorine,
Z is CO—NR$^6$, in which R$^6$ is H or C$_1$-C$_6$ alkyl,
PG is a vinyl group of the formula H$_2$C=C(—R$^9$)—
in which
R$^9$ is H or CH$_3$,
m is 1 or 2,
n is 1, 2, 3 or 4,
SP is absent or an (n+m)-valent linear or branched aliphatic C$_1$-C$_{30}$ radical in which the carbon chain can be interrupted by O, S, CO—NH, O—CO—NH or NH—CO—NH, an (n+m)-valent aromatic C$_6$-C$_{18}$ radical, an (n+m)-valent cycloaliphatic C$_3$-C$_{18}$ radical or an (n+m)-valent heterocyclic C$_3$-C$_{18}$ radical.

14. Dental material which contains
(a) 5 to 90 wt. % filler that is surface-modified with a compound of the formula (I),

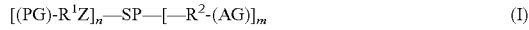
[(PG)-R$^1$Z]$_n$—SP—[—R$^2$-(AG)]$_m$     (I)

in which
AG is —SiR$^3$R$^4$X,
R$^1$ is a C$_1$-C$_3$ alkylene group or cyclopropylene group or is absent,
R$^2$ is a C$_1$-C$_{10}$ alkylene group or is absent,
R$^3$ is a C$_1$-C$_8$ alkyl group, chlorine or OR$^5$,
R$^4$ is a C$_1$-C$_8$ alkyl group, phenyl, chlorine or OR$^5$,
R$^5$ is a C$_1$-C$_6$ alkyl group,
X is OR$^5$ or chlorine,
Z is CO—NR$^6$, in which R$^6$ is H or C$_1$-C$_6$ alkyl,
PG is an allyl group, a styryl group, a vinyl cyclopropyl group or a radically polymerizable group of the formula

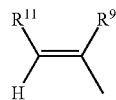

in which
R$^9$ is H, C$_1$-C$_3$ alkyl, C$_1$-C$_3$ hydroxyalkyl or COOR$^{10}$,
R$^{10}$ is H, C$_1$-C$_{10}$ alkyl, 1,6-dimethylphenyl or mesityl,
R$^{11}$ is H or phenyl,
m is 1 or 2,
n is 1, 2, 3 or 4,
SP is absent or an (n+m)-valent linear or branched aliphatic C$_1$-C$_{30}$ radical in which the carbon chain can be interrupted by O, S, CO—NH, O—CO—NH or NH—CO—NH, an (n+m)-valent aromatic C$_6$-C$_{18}$ radical, an (n+m)-valent cycloaliphatic C$_3$-C$_{18}$ radical or an (n+m)-valent heterocyclic C$_3$-C$_{18}$ radical, wherein the radicals can be substituted with a C$_1$-C$_5$ alkyl, Cl, Br and/or OH or unsubstituted,
(b) 9.9 to 90 wt.-% radically polymerizable monomer, and
(c) 0.1 to 5.0 wt.-% an initiator for the radical polymerization,
(d) 0 to 70 wt.-% solvent,
each relative to the total mass of the dental material.

15. Dental material according to claim 14, which contains at least one acidic monomer.

16. Dental material according to claim 14, wherein the dental material is an adhesive, filling composite, fixing cement, fissure sealer or coating material.

17. Dental material according to claim 1, wherein the filler is based on ZrO$_2$, Ta$_2$O$_5$, TiO$_2$, a mixed oxide of SiO$_2$, ZrO$_2$ and/or TiO$_2$, Yb$_2$O$_3$, Y$_2$O$_3$, YbF$_3$, Al$_2$O$_3$ and AlO(OH), boehmite, silicon oxide, glass ceramic or glass powder.

18. Dental material according to claim 5, wherein the filler is based on ZrO$_2$, Ta$_2$O$_5$, TiO$_2$, a mixed oxide of SiO$_2$, ZrO$_2$ and/or TiO$_2$, Yb$_2$O$_3$, Y$_2$O$_3$, YbF$_3$, Al$_2$O$_3$ and AlO(OH), boehmite, pyrogenic silica or precipitated silica.

19. Dental material according to claim 4, wherein the filler is based on an X-ray opaque metal compound.

20. Dental material according to claim 1, wherein the dental material is an adhesive, filling composite, fixing cement, fissure sealer or coating material.

21. Method of applying the dental material according to claim 1 to a patient's tooth or teeth for restoring the tooth or teeth.

22. Dental material comprising a filler that is based on Ta$_2$O$_5$, Yb$_2$O$_3$, Y$_2$O$_3$, YbF$_3$, silicon oxide, glass ceramic or glass powder and that is surface-modified with a compound of the formula (I),

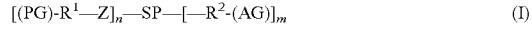
[(PG)-R$^1$—Z]$_n$—SP—[—R$^2$-(AG)]$_m$     (I)

in which
AG is —SiR$^3$R$^4$X,
R$^1$ is a C$_1$-C$_3$ alkylene group or cyclopropylene group or is absent,
R$^2$ is a C$_1$-C$_{10}$ alkylene group or is absent,
R$^3$ is a C$_1$-C$_8$ alkyl group, chlorine or OR$^5$,
R$^4$ is a C$_1$-C$_8$ alkyl group, phenyl, chlorine or OR$^5$,
R$^5$ is a C$_1$-C$_6$ alkyl group,
X is OR$^5$ or chlorine,
Z is CO—NR$^6$, in which R$^6$ is H or C$_1$-C$_6$ alkyl,
PG is an allyl group, a styryl group, a vinyl cyclopropyl group or a radically polymerizable group of the formula

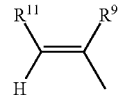

in which
R$^9$ is H, C$_1$-C$_3$ alkyl, C$_1$-C$_3$-hydroxyalkyl or COOR$^{10}$,
R$^{10}$ is H, C$_1$-C$_{10}$ alkyl, 1,6-dimethylphenyl or mesityl,
R$^{11}$ is H or phenyl,
m is 1 or 2,
n is 1, 2, 3 or 4,
SP is absent or an (n+m)-valent linear or branched aliphatic C$_1$-C$_{30}$ radical in which the carbon chain can be interrupted by O, S, CO—NH, O—CO—NH or NH—CO—NH, an (n+m)-valent aromatic C$_6$-C$_{18}$ radical, an (n+m)-valent cycloaliphatic C$_3$-C$_{18}$ radical or an (n+m)-valent heterocyclic $C_3$-$C_{18}$ radical, wherein the radicals can be substituted with a $C_1$-$C_5$ alkyl, Cl, Br and/or OH or unsubstituted.

23. Dental material according to claim 22, wherein the filler is based on silicon oxide, glass ceramic or glass powder.

24. Dental material according to claim 1, which contains 5 to 50 wt.-% filler that is based on an inorganic filler and that is surface-modified with a compound of the formula (I) relative to the total mass of the dental material.

25. Dental material according to claim 1, which contains 9.9 to 40 wt.-% radically polymerizable monomer relative to the total mass of the dental material.

26. Dental material according to claim 1, which contains 0.2 to 2.0 wt.-% initiator for the radical polymerization relative to the total mass of the dental material.

27. Dental material according to claim 1, which contains 0 to 50 wt.-% solvent relative to the total mass of the dental material.

28. Dental material according to claim 1, which contains
 (a) 5 to 50 wt.-% filler that is based on an inorganic filler and that is surface-modified with a compound of the formula (I),
 (b) 9.9 to 40 wt.-% radically polymerizable monomer,
 (c) 0.2 to 2.0 wt.-% initiator for the radical polymerization, and
 (d) 0 to 50 wt.-% solvent,
 each relative to the total mass of the dental material.

29. Dental material according to claim 9, wherein the acidic monomer is selected from the group consisting of 2-[4-(dihydroxyphosphoryl)-2-oxa-butyl]-acrylic acid ethyl ester, 2-[4-(dihydroxyphosphoryl)-2-oxa-butyl]-acrylic acid, 2-[4-(dihydroxyphosphoryl)-2-oxa-butyl]-acrylic acid-2,4,6-trimethylphenylester, 6-(N-acryloylamino)hexyldihydrogen phosphate, 6-(N-methacryloylamino)hexyldihydrogen phosphate, 1,3-bis-(N-acryloylamino)-propan-2-yl-dihydrogen phosphate and 1,3-bis-(N-methacryloylamino)-propan-2-yl-dihydrogen phosphate.

* * * * *